United States Patent [19]

Gold

[11] 4,444,206
[45] Apr. 24, 1984

[54] MESH TIP PACING LEAD ASSEMBLY

[75] Inventor: Philip Gold, Pompano Beach, Fla.

[73] Assignee: Cordis Corporation, Miami, Fla.

[21] Appl. No.: 373,081

[22] Filed: Apr. 29, 1982

[51] Int. Cl.³ .............................................. A61N 1/04
[52] U.S. Cl. .................. 128/784; 128/419 P
[58] Field of Search .................... 128/419 P, 784–786, 128/335.5

[56] References Cited

U.S. PATENT DOCUMENTS

| 2,985,172 | 5/1961 | Jones .................................... 128/416 |
| 3,683,933 | 8/1972 | Mansfield ........................ 128/419 P |
| 3,737,579 | 6/1973 | Bolduc ................................. 128/418 |
| 3,875,947 | 4/1975 | Jula et al. ............................ 128/418 |
| 3,892,648 | 7/1975 | Phillips et al. ................. 128/DIG. 8 |
| 3,911,928 | 10/1975 | Lagergren ........................... 128/418 |
| 3,935,864 | 2/1976 | Lagergren ........................... 128/418 |
| 4,010,758 | 3/1977 | Rockland et al. .................... 128/418 |
| 4,011,861 | 3/1973 | Enger ............................... 128/419 P |
| 4,030,509 | 6/1977 | Heilman et al. ................. 128/419 D |
| 4,149,542 | 4/1979 | Thoren ............................... 128/418 |
| 4,156,429 | 5/1979 | Amundson ...................... 128/419 P |
| 4,217,913 | 8/1980 | Dutcher .......................... 128/419 P |
| 4,281,669 | 8/1981 | MacGregor ..................... 128/419 P |
| 4,352,360 | 10/1982 | King ............................... 128/419 P |

Primary Examiner—William E. Kamm
Attorney, Agent, or Firm—Henry W. Collins; Thomas R. Vigil

[57] ABSTRACT

The pacing lead assembly includes an electrical conductor, for example, a flexible conductive wire, a terminal electrically connected to one end of the conductor, an insulative coating extending over a major portion of the length of the conductor, and an electrode coupled to the other end of the conductor. The electrode includes a conductive substrate having a smooth surface and being of generally a spherical configuration. The substrate is preferably covered by two layers of woven mesh screen which are bound onto the smooth surface of the substrate to thereby provide an electrode to which tissue from an organ to be stimulated may bond.

15 Claims, 2 Drawing Figures

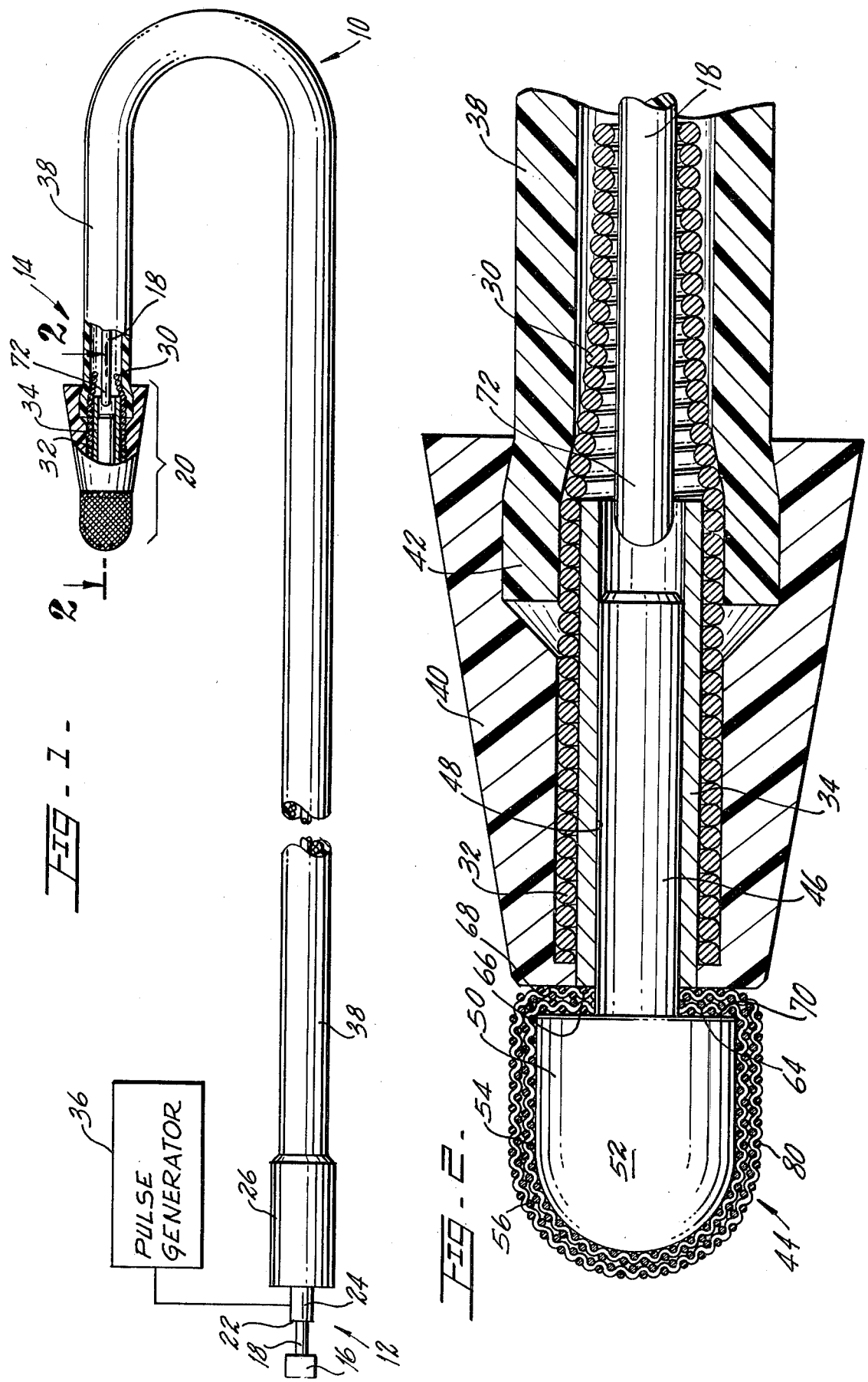

MESH TIP PACING LEAD ASSEMBLY

BACKGROUND OF THE INVENTION

The present invention relates to pacing leads for delivering electrical stimulation pulses to an organ, and more particularly to an improved pacing lead assembly having an electrode which is of a configuration to allow tissue from an organ to be stimulated to ingrow into the surface of the electrode to thereby anchor the electrode in a fixed position with respect to the organ.

Pacing leads generally comprise an electrode and a flexible insulative conductor for connecting an electrode to a pacer or a stimulator. In the case of cardiac pacing, the electrode is introduced through the vascular system into a cardiac cavity and is then moved into a position to contact the endocavitary wall of the heart. Various types of attaching devices are utilized to maintain the electrode in a fixed position with respect to the wall to be stimulated. For example, fins and tines are utilized to interlock in the trabeculi within the heart in order to prevent dislodgement of the electrode. Another type of pacing lead includes an electrode having a substrate which is coated with a plurality of small metal particles to form a network of interconnected pores over the surface of the electrode. Still another type of pacing lead includes an electrode in which a non-woven mesh material is placed over a mesh ball in order to form a porous tip.

Whenever a pacing lead is implanted, there is always the possibility that it will be desirable at some future date to withdraw or remove the lead from the organ to be stimulated. For example, it may become necessary to stimulate another part of the organ or it may be that the pacing lead has become damaged and must be replaced with a new lead.

In the case of the latter described pacing leads, which include an electrode formed of a mesh ball covered by a non-woven mesh screen, the surface formed of these materials serves to allow the ingrowth of soft tissue from the wall of the organ to be stimulated. When the tissue fibers have ingrown into the openings in the screen and mesh ball, the electrode is then retained in a fixed position with respect to the wall of the heart. One of the problems associated with this type of electrode construction is that the tissue fibers become so interwoven through the mesh screen and into the mesh ball, and it becomes very difficult to detach the electrode from the wall of an organ without causing localized damage to the organ. It is believed that the tissue fibers continue to grow and to become more interwoven throughout their entire length into the mesh ball thereby permanently bonding the fiber to the electrode. Accordingly, when one attempts to remove the pacing lead, it is necessary to literally tear the tissue fibers from the wall of the heart. Examples of prior implantable electrodes are disclosed in U.S. Pat. No. 4,156,429.

SUMMARY OF THE INVENTION

Turning now to the particular aspects of the present invention, the pacing lead assembly includes an electrical conductor, such as a flexible conductive wire, a terminal which is electrically connected to one end of the conductor which serves to connect the lead to a pacer, an insulative coating extending over a major portion of the length of the conductor and an electrode connected to the other end of the conductor. The electrode includes a substrate which has a smooth rigid outer surface and which is covered by two layers of woven mesh screen. The wire of the mesh screen can be approximately 0.001 inches and each layer of screen can have a thickness of approximately 0.0025 inches.

With this construction of the electrode, when the electrode is placed into contact with the wall of an organ to be stimulated, the soft tissue fibers ingrow into the woven mesh screen but are prevented from ingrowing into the screen beyond a predetermined depth established by the thickness of the layer or layers of screen.

As a result of this structural design, it is believed that the tissue fibers will ingrow to a sufficient depth to allow the electrode to be attached to the wall of an organ to be stimulated, however, the electrode may be subsequently detached from the wall of the organ for removal of the pacing lead without significant local damage to the organ.

Therefore, it is a primary object of the present invention to provide an improved implantable pacing lead assembly with an electrode structure which is particularly adapted for use in electrical stimulation of an organ, such as the heart. It is a further object of the present invention to provide an improved implantable pacing lead assembly with an electrode which becomes affixed to the wall of an organ but may be subsequently detached from the wall for replacement.

It is yet a further object of the present invention to provide an improved pacing lead assembly with an electrode configuration which takes the form of a woven mesh screen which covers a rigid smooth surface substrate wherein tissue fibers may ingrow into the mesh screen but are prevented from ingrowth beyond a predetermined depth.

Other and further objects of the present invention will become apparent to those skilled in the art upon a study of the following specification, appended claims and accompanying drawings.

BRIEF DESCRIPTION OF THE DRAWINGS

FIG. 1 is a plan view of a pacing lead assembly having a pervenous electrode assembly at the distal end thereof with the electrode assembly including an electrode tip made in accordance with the teachings of the present invention with portions broken away.

FIG. 2 is a sectional view of the pervenous electrode assembly shown in FIG. 1, is taken along line 2—2 of FIG. 1 and shows part of the electrode tip not in section.

DESCRIPTION OF THE PREFERRED EMBODIMENT(S)

Referring now to the drawings in greater detail, there is illustrated in FIG. 1 a pacing lead assembly 10 constructed in accordance with the teachings of the present invention. The pacing lead assembly 10 has a proximal end 12 and a distal end 14.

At the proximal end 12 is situated a plunger mechanism 16 that is connected to a flexible stylet 18 which extends through the pacing lead assembly 10 to a pervenous electrode assembly 20 at the distal end 14 of the assembly 10.

The flexible stylet 18 extends into a rear end 22 of a tubular terminal member 24 which is fixed within a flexure sleeve 26 and which is electrically connected to one end (hidden from view) of a coiled conductive wire 30 which extends like a coil spring around the stylet 18 to the pervenous electrode assembly 20 where a distal end 32 thereof is received around and in electrical contact with a tubular electrode 34 of the electrode assembly 20.

As shown, the tubular member 24 is electrically connected to a pulse generator 36 which is operable to supply electrical pulses to the terminal member 24 for transmission to the electrode assembly 20. Also, as shown, the coiled conductive wire 30 is surrounded by an insulative sheath 38 which extends between the flexure sleeve 26 and the electrode assembly 20.

Referring now to FIG. 2, the pervenous electrode assembly 20 includes a frustoconical insulating member 40 which surrounds the distal end 32 of the coiled conductive wire 30 and tubular electrode 34 as shown. The insulating member 40 has a cavity in the base thereof through which the distal end 32 of wire 30 extends and in which distal end 42 of sheath 38 is received.

The electrode assembly 20 includes an electrode tip 44 having a shank 46 which is frictionally received in and in electrical contact with the interior 48 of the tubular electrode 34.

As will now be described below, the electrode tip 44 is constructed in accordance with the teachings of the present invention as will be described hereinafter.

In addition to the cylindrical shank 46 frictionally and electrically received within the tubular electrode 34, the electrode tip 44 includes a bullet shaped head 50 which has a smooth outer, substrate-forming surface 52 thereon.

At least one, and in the illustrated embodiment two, layers 54 and 56 of mesh wire screen are conformed or molded about the bullet shaped head 50 to form a porous shell 58 about the head 50 in accordance with the teachings of the present invention. It may even be desirable to have three layers of mesh wire screen although two appear to be satisfactory for providing a structure into which tissue can grow after the electrode tip 44 has been pushed into an endocavitary wall of an organ while enabling the electrode tip 44 to be withdrawn with minimal tearing of the fibrous tissue growth around and in the layers 54 and 56 of mesh wire screen.

The layer or layers 54 and 56 can be fused to the bullet shaped head 50 or folded behind the head 50 where the diameter of tip 44 reduces to the diameter of the shank 40 and then held in place by a press fit of the electrode tip 44 into the tubular electrode 34 with folded portions 64 and 66 of the layers 54 and 56 being clamped between an an annular front face 68 of the frustoconical insulating member 40 (and outer end of tubular electrode 34) and an annular shoulder 70 of the head 50.

The layers 54 and 56 of fine wire cloth or mesh screens are made of platinum or other suitable material and are formed over or pressed over the bullet shaped head 50 and in electrical contact therewith. The layers 54 and 56 of screen form a network of interstices for controlled tissue ingrowth when the electrode tip 44 is implanted into an endocavitary wall, such as in the endocardium or myocardium of a heart. This is accomplished by moving the plunger mechanism 16 inwardly to cause distal end 72 of stylet 18 to engage the shank 46 for pushing the electrode tip 44, namely head 50 with layers 54 and 56 thereon, into an endocavitary wall.

The above described construction of the tip 44 enables it to be implanted in an endocavitary wall in such a manner that tissue ingrowth into the double layered mesh screen 54 and 56 can quickly secure the electrode tip 44 in place to reduce the possibility of early dislodgement from the endocavitary wall. Yet, at the same time, the provision of only two (possibly one or three) layers 54 and 56 of mesh wire screen limit the depth of ingrowth of the fibrous tissue into the electrode tip 44, such ingrowth stopping at the substrate surface 52 so that removal of the electrode tip 44, and for that matter the whole pacing lead assembly 10, can be accomplished with minimum tearing of tissue growth from the organ, e.g., the heart.

The fine wire 80 in each layer 54 or 56 of mesh screen can have a diameter of approximately 0.001 inch with a thickness between the top and bottom of a layer of screen being approximately 0.0025 inch. Thus, with shell 50 of two layers 54 and 56 of mesh wire screen over the head 50, the thickness from the substrate surface 52 of the head 50 to the outer envelope of the layer 56 of wire mesh screen is approximately 0.005 inch.

If the layer or layers 54 and 56 of mesh wire screen is or are not clamped in the manner shown in FIG. 2, but rather are fused to head 50, then the electrode tip 44 with the shell of one, two or three layers 54, 56 of mesh wire screen can be formed around the bullet shaped head 50 and placed in a hydrogen or argon atmosphere where the layers 54, 56 are fused to the substrate surface 52.

In use, the pacing lead assembly 10 is inserted into a vein until the pervenous electrode assembly 20 at the distal end 14 thereof reaches the endocardial cavity. At that point, the plunger mechanism 16 is moved a predetermined distance to move the distal end 72 of the stylet 18 against the rear end of the shank 46 to push the electrode tip 44 into the endocavitary wall until the head 50 is firmly embedded, such as in the myocardium. Then, if it later should become necessary or desirable to remove the pacing lead assembly 10, the prevenous electrode assembly 20 can be withdrawn from the endocavitary wall with some of the fibrous tissue growth ripping and some pulling out of the single or multilayered mesh wire screen, i.e., layers 54 and 56, thereby minimizing trauma to the myocardium and/or endocardium.

It will be appreciated that the electrode tip 44 can be utilized in other permanent prosthetic systems where permanent or semipermanent attachment to body tissue or bone is required. By varying the number of layers 54, 56, the wire 80 diameter, and the mesh size to control the porous area, the permanency can be controlled. This is especially true where vascularization is to be controlled. Some examples where the electrode tip 44 can be utilized are bone grafts, dental implants or housings for artificial organs.

Moreover, it is to be understood that the mesh screen can be made of other suitable materials besides platinum. For example, the fine wire could be made of highly body-compatible plastics. It may even be made of a biological substance which is biodegradable. In this respect, some studies indicate that collagen might be a suitable material. However, other studies indicate that more scar tissue is developed than the original volume of the collagen substance used in the shell 50 and for this reason may not be suitable.

Additionally, it may be desirable to coat the layers 54, 56 of mesh wire screen with a collagen attachment factor, such as fibronectin, to enhance and speed up the growth of collagen into and around the shell 50.

From the foregoing description it will be apparent that the pacing lead assembly 10 of the present invention and more particularly the electrode tip 44 of the pervenous electrode assembly 20 thereof provide a number of advantages, some of which have been described above and others of which are inherent in the invention.

Also, it will be apparent to those skilled in the art that modifications can be made to the pacing lead assembly 10 of the present invention without departing from the teachings of the invention. Accordingly, the scope of the invention is only to be limited as necessitated by the accompanying claims.

I claim:

1. A pacing lead assembly comprising: a terminal member adapted to be electrically coupled to a pulse generator, an electrode assembly, an electrically conductive flexible wire connected at one end to said terminal member and at the other end to said electrode assembly, an insulative coating extending over a major portion of the length of said flexible wire, and said electrode assembly including a body, an electrode tip including a head having a smooth outer surface and a shank, and a thin porous shell around and in electrical contact with said smooth outer surface thereby to form interstices within which tissue from an organ to be stimulated may bond but with tissue ingrowth being limited by the thickness of said shell, said shank being received in a socket in the distal end of said body, and said shell comprising at least two layers of mesh wire screen with a portion of said layers being received behind said head and clamped between said head and said body.

2. The pacing lead assembly of claim 1 wherein each layer of mesh wire screen is made of wire approximately 0.001 inch thick.

3. The pacing lead assembly of claim 1 wherein said shell is approximately 0.0025 inch thick.

4. The pacing lead assembly of claim 1 wherein said layers of mesh wire screen are made of wire approximately 0.001 inch thick.

5. The pacing lead assembly of claim 1 wherein said layers of mesh wire screen are made of platinum wire.

6. The pacing lead assembly of claim 1 wherein said layers of mesh wire screen are made of a highly body-compatible plastic.

7. The pacing lead assembly of claim 1 wherein said layers of mesh wire screen are coated with a collagen attachment factor.

8. The pacing lead assembly of claim 7 wherein said collagen attachment factor is fibronectin.

9. The pacing lead assembly of claim 1 wherein said electrode tip has a bullet shaped head and wherein said smooth outer surface is on said head.

10. The pacing lead assembly of claim 1 wherein said shank is electrically coupled through said socket to said wire.

11. The pacing lead assembly of claim 10 wherein said electrode assembly includes a tubular electrode having said wire in electrical contact with the outer surface thereof defining said socket therein and having said shank of said electrode tip frictionally received therein and in electrical contact therewith.

12. The pacing lead assembly of claim 11 wherein said electrode assembly includes an insulative member around said tubular electrode.

13. The pacing lead assembly of claim 12 wherein said portion of said layers of mesh wire screen are received behind said head and clamped between said head and the outer end of said tubular electrode and/or an outer face of said insulative member by press fitting said tip electrode into said tubular electrode.

14. The pacing lead assembly of claim 11 including a flexible stylet extending from said terminal member to said electrode assembly and having a plunger mechanism at the proximal end thereof for moving said stylet and having a distal end adapted to engage the rear end of said shank for pushing said shank thereby to push said head into an endocavitary wall of an organ.

15. The pacing lead assembly of claim 1 wherein at least the inner layer of mesh wire screen is fused to said smooth outer surface of said head.

* * * * *